United States Patent [19]
Mehdizadeh

[11] Patent Number: 5,928,284
[45] Date of Patent: Jul. 27, 1999

[54] DISC REPLACEMENT PROSTHESIS

[76] Inventor: Hamid M. Mehdizadeh, 14928 Diduca Way, Los Gatos, Calif. 95032

[21] Appl. No.: 09/112,865

[22] Filed: Jul. 9, 1998

[51] Int. Cl.⁶ .............................. A61F 2/44; A61F 2/28; A61F 2/02; A61B 17/56
[52] U.S. Cl. ............................... 623/17; 623/16; 623/11; 606/61; 3/1.91
[58] Field of Search ................................ 623/17, 13, 18, 623/16; 606/61

[56] References Cited

U.S. PATENT DOCUMENTS

| | | | |
|---|---|---|---|
| 4,309,777 | 1/1982 | Patil | 3/1.91 |
| 4,743,256 | 5/1988 | Brantigan | 623/17 |
| 5,015,247 | 5/1991 | Michelson | 606/61 |
| 5,674,296 | 10/1997 | Bryan et al. | 623/17 |
| 5,702,450 | 12/1997 | Bisserie | 623/17 |

OTHER PUBLICATIONS

Kevin Gill, M.D., Ray Threaded Fusion Cage: Clinical Results at Two Years. Feb. 22, 1996. pp. 1 of 1, 1 of 1 and 1, 2 and 3 of 3.

Author Unknown, Part I Removal of Disc, Part II Posterior Lumbar Interbody Fusion. Post 1970, pp. 1–15.

Neal I. Aronson, M.D. et al, Anterior Cervical Dislectomy and Fusion: Smith–Robinson Approach, 1982. pp. 1–5.

*Primary Examiner*—Mickey Yu
*Assistant Examiner*—Alvin Stewart
*Attorney, Agent, or Firm*—H. M. Stanley

[57] ABSTRACT

A disc replacement prosthesis is described which is placed within the intradiscal space vacated by a removed deteriorated disc, and which affords mobility rather than fusion between adjacent vertebral bodies. The prosthesis also protects remaining discs from deterioration by providing a shock absorbing prosthesis portion. It adheres initially mechanically to the vertebral bodies and adheres through arthrodesis over a period of time.

10 Claims, 2 Drawing Sheets

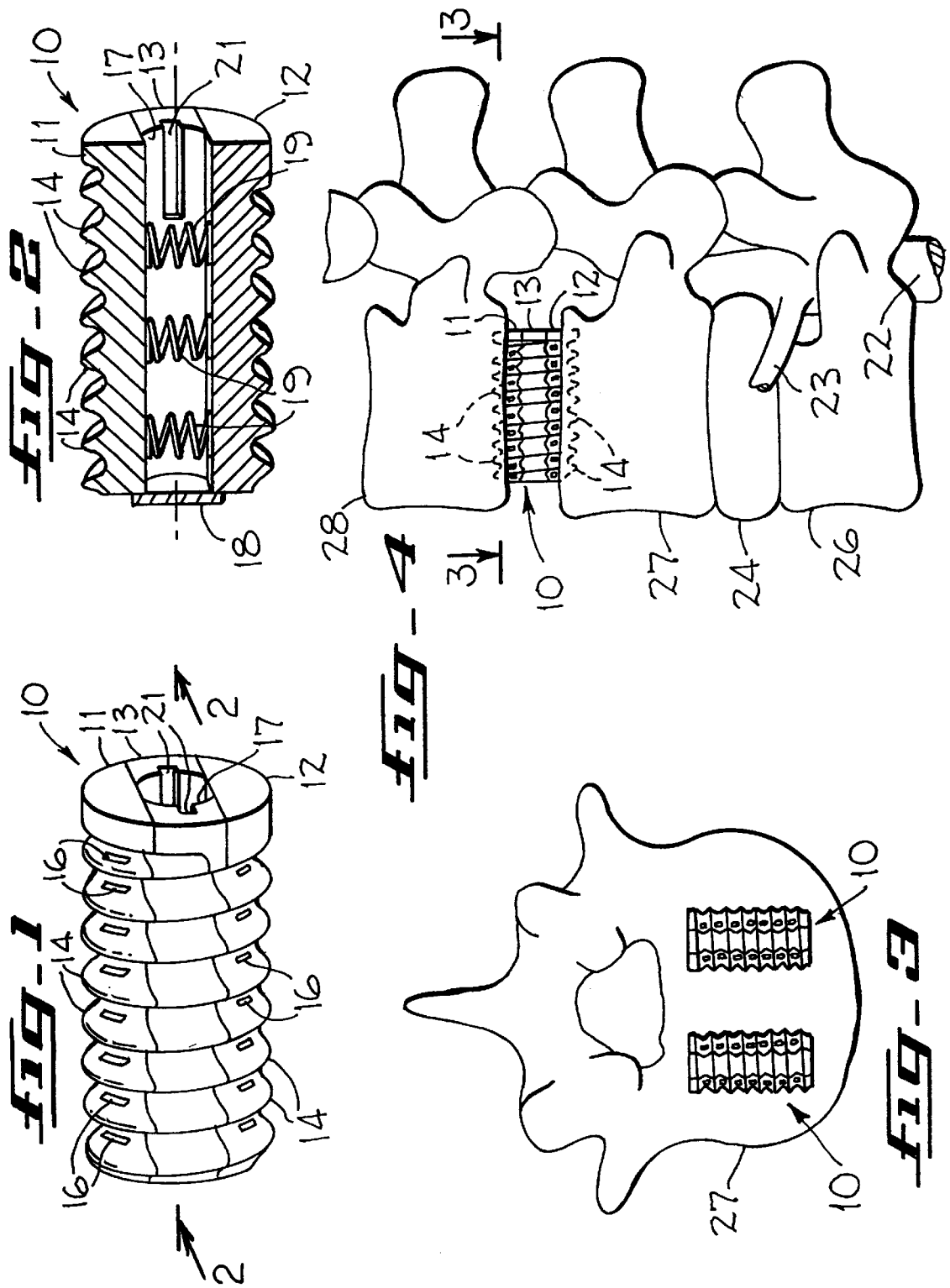

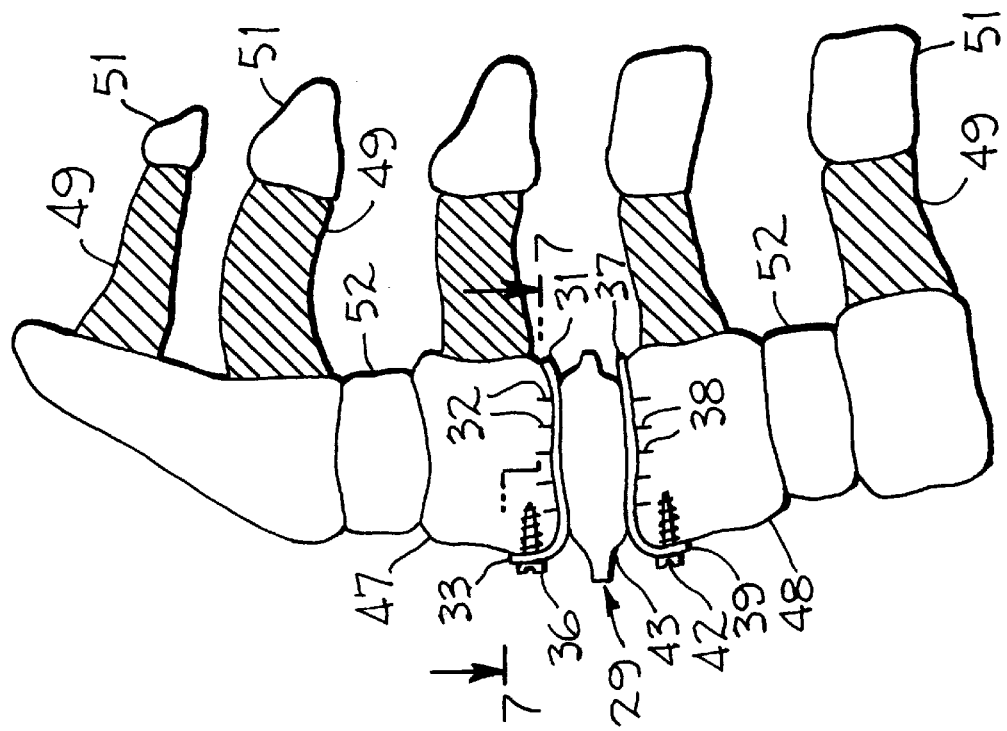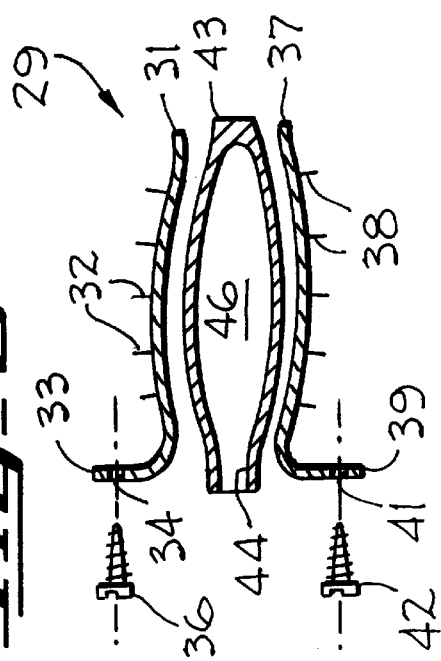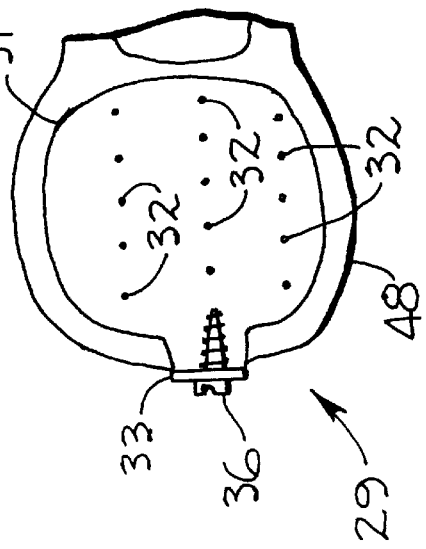

DISC REPLACEMENT PROSTHESIS

SUMMARY OF THE INVENTION

A disc replacement prosthesis is described for positioning between adjacent superior and inferior vertebral bodies in the spine. Included is an upper cylindrical section for contacting and gripping the superior vertebral body lower surface and a lower cylindrical section for contacting and gripping the inferior vertebral body upper surface. A resilient intermediate cylindrical section is affixed to and extends between the upper and lower means for contacting and gripping. The upper, intermediate and lower sections form a cylinder having an exterior surface when joined, and screw threads are formed on the exterior surface of the cylinder.

The invention described herein includes a method of providing a prosthetic replacement for a vertebral disc removed from an intradiscal space between adjacent superior and inferior vertebral bodies wherein the inferior and superior vertabral bodies are tapped to form screw threads adjacent the intradiscal space. The method includes the steps of fabricating an upper and a lower rigid member having surfaces thereon which are porous to living bone cells, and configuring the upper and lower rigid members to have external screw threads matching the screw threads on the superior and inferior vertabral bodies for retention by the adjacent superior and inferior vertabral bodies respectively. Further included are the steps of attaching a resilient member between the upper and lower rigid members to produce a disc prosthesis engaging the disc prosthesis external screw threads with the vertabral body screw threads, and turning the disc prosthesis on the threads until positioned within the intradiscal space.

In accordance with the invention described herein a prosthesis is disclosed for replacing a disc removed from an intradiscal space between adjacent superior and inferior vertebral bodies. An upper prosthesis cylindrical section is included having a contact surface configured to engage and become fixed to a lower surface on the superior vertebral body. Furthermore, a lower prosthesis cylindrical section is included having a contact surface configured to engage and become fixed to an upper surface on the inferior vertebral body. An intermediate elastomeric prosthesis cylindrical section is fixed to and extends between the upper and lower prosthesis cylindrical sections. The upper, intermediate and lower cylindrical sections form a cylinder when joined. The cylinder has a cylindrical surface having screw threads formed theron for securing the upper and lower prosthesis cylindrical sections in place and in contact with the superior and inferior vertebral bodies, respectively. The upper and lower prosthesis member contact surfaces have a porosity for admitting bone cell growth for enhancing arthrodesis.

BRIEF DESCRIPTION OF THE DRAWINGS

FIG. 1 is a perspective of one embodiment of the present invention.

FIG. 2 is a section along the line 2—2 of FIG. 1.

FIG. 3 is a section along the line 3—3 of FIG. 4.

FIG. 4 shows the embodiment of FIG. 1 disposed between adjacent vertebral bodies.

FIG. 5 is an exploded section of an additional embodiment of the present invention.

FIG. 6 shows the embodiment of FIG. 5 disposed between adjacent vertebral bodies.

FIG. 7 is a section along the line 7—7 of FIG. 6.

DESCRIPTION OF THE PREFERRED EMBODIMENTS

The history of surgical procedures for correction of spinal deformity goes back many years and, when the procedures relate to problems caused by intravertrabral disc deterioration, always include fusion of two or more vertebrae through the use of rods, clamps, wires, bone plugs, and various other intradiscal space fusion devices. The purpose in these procedures has always been to immobilize two or more vertebrae to remove or reduce pain emanating from pressure on the cauda equina or nerve roots extending therefrom. By way of example, a nerve root retractor and disc space spreader is described and claimed in the applicant's U.S. Pat. No. 5,803,904 issued Sep. 8, 1998, which is useful in a surgical procedure for implanting a threaded fusion cage in the intradiscal space vacated by a removed disc. The nerve root retractor of the aforementioned application is also useful, together with the other instruments described therein, for placing the embodiment of the present invention as seen in FIG. 1 between adjacent vertebral bodies within the vacated intradiscal space. Previous to the advent of the present invention when a vertebral disc was removed and adjacent vertebral bodies fused, deterioration of the remaining discs in the spinal column occurred because the cumulative shock absorption capability of the spine was reduced by removal of one of the spine's shock absorbing components, the disc. In all cases of vertebral fusion, accelerated deterioration of remaining discs is inevitable. It may be seen from the following description that through the use of the invention disclosed and claimed herein, not only is it possible to relieve pressure on the cauda equina and the nerve roots, but it is also possible to replace a removed disc and retain the shock absorbing characteristics of the replaced disc.

Referring to FIG. 1 of the drawings, a disc replacement prosthesis 10 is shown having an upper rigid member 11 and a lower rigid member 12. An intermediate resilient portion 13 is shown extending between and attached to the upper and lower rigid members 11 and 12. The intermediate portion 13 is fabricated of some body compatible material such as polypropylene or silicone elastomer. The upper and lower members 11 and 12, respectively, are formed of titanium or Hedrocel™ material in a preferred embodiment. The upper, lower and intermediate members shown in FIG. 1 are fixed together as by a body compatible cement to form a cylindrical prosthesis. The outer surface of the prosthesis 10 has screw threads 14 formed thereon and also has holes 16 extending through rigid members 11 and 12 which communicate with an axial channel 17 extending along the length of the prosthesis 10. The channel 17 may extend along the entire axial length of the prosthesis 10, or it may be capped at one end as shown by the cap 18 (FIG. 2), or it may only extend part way along the axial length of the prosthesis according to the surgical purposes for which the prosthesis is used. For example, additional vertical stiffness may be imparted to the prosthesis for upward and downward forces exerted against the lower and upper rigid portions 12 and 11, respectively, by filling the channel 17 with additional body compatible elastomeric substance and retaining it within the channel 17 by use of the cap 18 at one or both ends of the channel. Alternatively, as seen in FIG. 2, a selectable level of vertical stiffness is obtainable with a series of coil springs 19 affixed between the upper and lower rigid members 11 and 12 as by welding opposing ends of the springs 19 to the rigid members. Additionally, variable vertical stiffness from prosthesis to prosthesis is obtainable when the body compatible elastomeric substance is used in conjunction with the coil springs 19. As further seen in FIGS. 1 and 2, a proximal end of the prosthesis 10 has a to configuration such as the opposed interior key ways 21 for engagement by a cage insertion instrument during placement within the intradiscal space as is known in the threaded fusion cage surgical process. A known vertebral drill and vertebral tap are used together with the nerve root retractor and disc space spreader of the aforementioned invention described and claimed in U.S. Pat. No. 5,803,904 to place the prosthesis 10 within the intradiscal space as shown in FIG. 4 of the drawings. FIG. 4 also shows a portion of the cauda equina 22 with a nerve root 23 extending therefrom past a healthy disc 24 situated between a vertebral body 26 and a vertebral body 27. The prosthesis 10 is shown situated below and having upper rigid member 11 in contact with a lower threaded surface on a superior vertebral body 28. In like fashion, the threaded portion of lower rigid member 12 is in contact with an upper threaded surface on the inferior vertebral body 27 in FIG. 4. The aforementioned lower and upper surfaces of the adjacent vertebral bodies 28 and 27, respectively, have been tapped by the aforementioned vertebral tap to place threads therein which match the threads 14 on the prosthesis 10. The prosthesis is seen to be placed in FIG. 4 so that vertical force exerted thereupon will be absorbed by the resilient member 13 and any elastomeric filling substance within channel 17 or the coil springs 19 carried within channel 17.

With reference to FIG. 3, it may be seen that the prosthesis 10 is used in pairs to provide stability in the spinal column. As a result, mobility is retained between the vertebral bodies 27 and 28 rather than fusion and remaining discs, such as disc 24, are protected from deterioration because the pair of prostheses 10 (FIG. 3) retain most of the shock absorbing characteristics of the natural disc which they replace. While the prosthesis 10 is seen to be useful for replacement of discs in the lumbar region of the spine, it is envisioned that it may be used in other portions of the spine as well.

Referring now to FIG. 5 of the drawings, an exploded elevation of an alternative embodiment of the prosthesis of the present invention is shown at 29. An upper member or metallic plate 31 is shown having an upper surface from which a number of upwardly extending pins 32 about 2 mm long project. Upper metallic member 31 also has a tab 33 with a hole 34 therethrough for receiving a screw 36. A lower metallic member or plate 37 is shown having a number of short pins 38 about 2 millimeters long extending downward therefrom. In like fashion, the lower metallic plate 37 has a downwardly extending tab 39 having a hole 41 therethrough for receiving a screw 42. The upper and lower metallic plates 31 and 37 are fabricated from titanium or Hedrocel™ material as mentioned hereinbefore for the metallic cylindrical sections 11 and 12 in the embodiment of FIG. 1. The plates 31 and 37 fabricated from titanium material are hydroxy apatite treated to provide a surface which is porous to growing bone cells. Hedrocel™ material is useful for fabricating the plates 31 and 37 as it also provides a surface which is porous to living bone cells.

Continuing with the description of the embodiment of FIG. 5 showing the prosthesis 29, a bag of a material which is body compatible such as polypropylene is shown at 43. The bag has an opening 44 at one end through which an elastomeric substance may be deposited within a chamber 46 contained within the bag.

With reference to FIG. 6, the prosthesis 29 is shown in place between the lower surface of a superior vertebrae 47 and the upper surface of an inferior vertebrae 48. FIG. 6 shows a cervical portion of the spine wherein shaded areas 49 represent bone and cartilage extending from the anterior portions of the vertebral bodies 47 and 48 toward posterior portions 51. The anterior portions of the vertebral bodies are of interest in this disclosure and healthy non-deteriorated discs 52 are shown in place between some of the vertebral bodies in FIG. 6.

Upper plate 31 is shown in FIG. 6 attached by the screw 36 through the tab 33 to the superior vertebral body 47. The pins 32 are shown penetrating the lower surface of the superior vertebral body 47 to assist in fixing the metallic plate 31 in place initially before the bone cells are afforded an opportunity to grow into the porous surface of the plate.

In FIG. 6 the lower metallic plate 37 is shown fixed to the upper surface of the inferior vertebral body 48 by means of the screw 42 through the tab 39 and the pins 38 projecting downwardly from the metal plate 37 into the structure of the inferior vertebral body 48. The screws 36 and 42 are shown being introduced into the anterior portion of the vertebral bodies 47 and 48 because operations in the cervical portion of the spine are generally through an anterior opening. In like fashion, the opening 44 in the bag 43 is shown in the anterior portion of the bag so that the elastomeric material may be injected into the chamber 46 within the bag and the opening 44 sealed from the front. The upper surface of the bag 43 is fixed by a body compatible adhesive to the lower surface of the upper plate 31 and the lower surface of the bag 43 is fixed by such an adhesive to the upper surface of the lower plate 37. Once the cushion afforded by the bag 43 is appropriately filled and sized vertically and the opening 44 is sealed, the edges of the bag 43 are trimmed to cause the cushion to lie within the confines previously occupied by the removed deteriorated disc. As stated hereinbefore for the embodiment of the prosthesis shown in FIGS. 1 and 2, the prosthesis 29 shown in FIGS. 5, 6 and 7 protects healthy discs 52 by affording the shock absorbing capabilities of the replaced disc and also by affording mobility between the superior vertebral body 47 and the inferior vertebral body 48 rather than fusion therebetween. The prosthesis as finally installed is seen in FIG. 7 to occupy that space normally taken up by the replaced disc. Following temporary retention in place by the pins 32 and the screws 37 and 42, the prosthesis 29 is held securely by bone cell growth within the surface of the plates 31 and 32 whether they be hydroxy apatite treated titanium or Hedrocel™ material.

As recited hereinbefore, the method of providing a prosthetic replacement for a vertebral disc removed from an intradiscal space between adjacent superior and inferior vertebrae includes treating an upper and a lower rigid member to produce a surface thereon which is porous to living bone cells. Subsequent attachment of a resilient member between the upper and lower metallic members produces a disc prosthesis. The disc prosthesis is placed in the intradiscal space in contact with the adjacent vertebral bodies and secured in place, at least temporarily, by mechanical means. The resilient portion of the prosthesis may thereafter be filled with a body compatible elastomeric substance. The mechanical securing of the metallic portions of the prosthesis is obtained by the screw threads of the prosthesis 10 of FIGS. 1 and 2 or by the pins 32 and 38 and the screws 36 and 42 of the prosthesis 29 of FIGS. 5, 6 and 7. While the prostheses 10 and 29 have been described as useful in the lumbar and cervical regions of the spine respectively, their use is envisioned as possible in any region of the spine when appropriate.

Although the best mode contemplated for carrying out the present invention has been shown and described herein, it will be understood that modification and variation may be made without departing from what is regarded to be the subject matter of the invention.

What is claimed:

1. A disc replacement prosthesis for positioning between adjacent superior and inferior vertebral bodies in the spine comprising upper means for contacting and gripping the superior vertebral body lower surface, lower means for contacting and gripping the inferior vertebral body upper surface, resilient intermediate means affixed to and extending between said upper and lower means for contacting and gripping, wherein said upper means comprises an upper cylindrical section, said lower means comprises a lower cylindrical section, and said resilient intermediate means comprises an intermediate cylindrical section, said upper cylindrical section, lower cylindrical section and intermediate cylindrical section forming a cylinder having an exterior surface when joined together, further comprising screw threads on said exterior surface, the disc replacement prosthesis thereby being configured for positioning and retention between the adjacent superior and inferior vertebral bodies.

2. The disc replacement prosthesis of claim 1 comprising spring means fixed to and extending between said upper and lower cylindrical sections.

3. The disc replacement prosthesis of claim 2 wherein said spring means comprises a plurality of coil springs in parallel with said intermediate cylindrical section.

4. The disc replacement prosthesis of claim 1 wherein said intermediate cylindrical section has a channel extending axially therealong configured to receive a prosthesis insertion instrument.

5. The disc replacement prosthesis of claim 1 wherein said intermediate cylindrical section has a channel extending axially therealong, comprising body compatible elastomeric substance within said channel.

6. The disc replacement prosthesis of claim 1 wherein said upper and lower means for contacting and gripping comprise hydroxy apatite treated metallic members.

7. The disc replacement prosthesis of claim 1 wherein said upper and lower means for contacting and gripping comprise members having a surface porosity for promoting bone cell growth therewithin.

8. A method of providing a prosthetic replacement for a vertebral disc removed from an intradiscal space between adjacent superior and inferior vertebral bodies, wherein the superior and inferior vertabral bodies are tapped to form screw threads adjacent the intradiscal space, and a disc prosthesis has matching external screw threads thereon, comprising the steps of fabricating an upper and a lower rigid member having surfaces thereon which are porous to living bone cells, configuring the upper and lower rigid members for at least temporary retention by the adjacent superior and inferior vertebral bodies respectively, attaching a resilient member to and between the upper and lower rigid members to produce a disc prosthesis, engaging the disc prosthesis external screw threads with the vertebral body screw threads, and turning the disc prosthesis until positioned within the intradiscal space.

9. A prosthesis for replacing a disc removed from an intradiscal space between adjacent superior and inferior vertebral bodies, comprising an upper prosthesis member having a contact surface configured to engage and become fixed to a lower surface on the superior vertebral body, a lower prosthesis member having a contact surface configured to engage and become fixed to an upper surface on the inferior vertebral body, an intermediate elastomeric prosthesis member fixed to and extending between said upper and lower prosthesis members, and means for securing said upper and lower prosthesis members in place in contact with the superior and inferior vertebral bodies respectively, said upper and lower prosthesis member contact surfaces having a porosity for admitting bone cell growth for enhancing arthrodesis, wherein said upper prosthesis member comprises an upper cylindrical section, said lower prosthesis member comprises a lower cylindrical section and said intermediate elastomeric prosthesis member comprises an intermediate cylindrical section, so that the prosthesis is a cylinder having a cylindrical surface, said means for securing comprising screw threads on said cylindrical surface.

10. The prosthesis of claim 9 wherein said intermediate elastomeric member has an internal chamber, comprising resilient shock absorbing means within said internal chamber.

* * * * *